United States Patent [19]

Hofheinz et al.

[11] 4,366,166
[45] Dec. 28, 1982

[54] FILARICIDAL 2-NITROIMIDAZOLE COMPOUNDS

[75] Inventors: Werner Hofheinz, Bottmingen; Harro Stohler, Binningen, both of Switzerland

[73] Assignee: Hoffmann-La Roche Inc., Nutley, N.J.

[21] Appl. No.: 263,612

[22] Filed: May 14, 1981

[30] Foreign Application Priority Data

May 23, 1980 [CH] Switzerland .................. 4057/80

[51] Int. Cl.³ .................. A61K 31/415; C07D 233/91
[52] U.S. Cl. .................. 424/273 R; 548/336; 548/338
[58] Field of Search .................. 548/336, 338; 424/273 R

[56] References Cited

U.S. PATENT DOCUMENTS

| | | | |
|---|---|---|---|
| 3,391,156 | 7/1968 | Beaman et al. | 548/338 |
| 3,641,047 | 2/1972 | Beaman et al. | 548/338 |
| 3,679,698 | 7/1972 | Beaman et al. | 548/338 |

FOREIGN PATENT DOCUMENTS

| | | | |
|---|---|---|---|
| 1034126 | 7/1978 | Canada | 548/338 |
| 1695131 | 10/1970 | Fed. Rep. of Germany | 548/338 |

*Primary Examiner*—Richard A. Schwartz
*Attorney, Agent, or Firm*—Jon S. Saxe; George M. Gould; John J. Maitner

[57] ABSTRACT

2-Nitroimidazoles having filaricidal activity of the formula

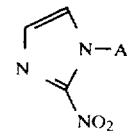

I wherein
A is one of the groups

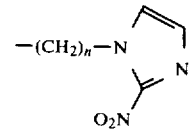

—C(R³)=C(R¹)(R²), —CHBr—CH₂Br or —CH₂—CCl=CH₂;
n is 1, 2, 3 or 4;
R¹ and R² are hydrogen or $C_{1-3}$-alkyl and
R³ is hydrogen, $C_{1-3}$-alkyl, chlorine or bromine, and
processes for their preparation are described. The compounds of formula I and compounds of formula

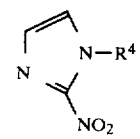

VII wherein R⁴ is —CH₂—CH₂OH, —CH₂—CHOH—CH₂OCH₃, —CH₂—CHOH—CH₂OH or

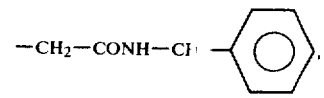

are useful in the treatment of filariasis is also described.

1 Claim, No Drawings

FILARICIDAL 2-NITROIMIDAZOLE COMPOUNDS

DETAILED DESCRIPTION OF THE INVENTION

Filaria are filiform worm parasites and are the cause of various diseases, particularly in Africa, Central and South America, India, China and South East Asia. Worldwide many millions of human beings suffer different manifestations of these diseases which have been grouped under the designation filariasis.

Heretofore, very few agents were available for the chemotherapy of filariasis. Only suramin, with activity to adult filaria (macrofilaria), and diethylcarbamazine, with activity to filaria larvae (microfilaria), were available for treatment of filariasis. Neither of these agents represent optimal chemotherapeutics against these infectious diseases since both medicaments exhibit a number of undesirable and to some extent dangerous side effects, such as, for example, kidney toxicity or allergic reactions. In the last 30 to 40 years very little if any progress has been made in the chemotherapy of these diseases, and no novel medicaments have been developed during the last 25 years. Therefore, filariasis represents a group of tropical diseases against which novel medicaments are urgently required.

It has now been discovered that novel 2-nitroimidazole compounds of the formula

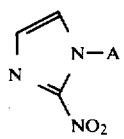

I wherein
A is one of the groups

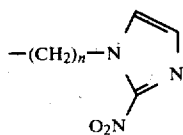

—C($R^3$)=C($R^1$)($R^2$), —CHBr—CH$_2$Br or —CH$_2$—CCl=CH$_2$;
n is for 1, 2, 3 or 4;
$R^1$ and $R^2$ are hydrogen or C$_{1-3}$-alkyl and
$R^3$ is hydrogen, C$_{1-3}$-alkyl, chlorine or bromine,
are suitable for the chemotherapy of filariasis and can accordingly be used as medicaments in the treatment thereof.

Furthermore, it has been discovered that known 2-nitroimidazole compounds of formula VII

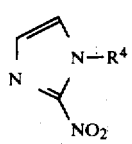

VII wherein $R^4$ is —CH$_2$—CH$_2$OH, —CH$_2$—CHOH—CH$_2$OCH$_3$, —CH$_2$—CHOH—CH$_2$OH or

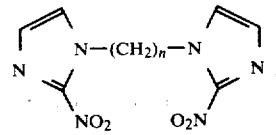

can also be utilized for the chemotherapy of filariasis.

Formula I includes the two following types of compound:

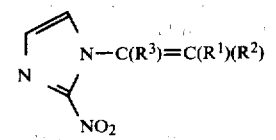

Ia wherein n is 1, 2, 3 or 4, and

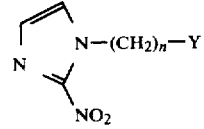

Ib wherein
$R^1$ and $R^2$ are hydrogen or C$_{1-3}$-alkyl and
$R^3$ is hydrogen, C$_{1-3}$-alkyl, chlorine or bromine,
as well as 1-(1,2-dibromoethyl)-2-nitroimidazole and 1-(2-chloroallyl)-2-nitroimidazole.

Preferred compounds of formula I are 1,2-ethylene-bis-(2-nitroimidazole) and 2-nitro-1-vinylimidazole.

The 2-nitroimidazole compounds of formula I are prepared by one of the procedures described hereinafter.

PROCEDURE A

Reacting azomycin with a disubstituted aliphatic hydrocarbon of the formula Y—(CH$_2$)$_n$—Y or Y—CH$_2$—CCl=CH$_2$, wherein Y represents halogen, such as chlorine, bromine or iodine, or another cleavable group, such as tosyloxy. In compound Y—(CH$_2$)$_n$—Y the two symbols Y can be the same or can differ from one another. The reaction is conveniently carried out in the presence of a suitable inert organic solvent. Suitable solvents for this reaction include dimethylformamide, dimethylacetamide or methylene chloride. The reaction may be carried out at a temperature between room temperature and the reflux temperature of the reaction mixture. Furthermore, the reaction may be carried out in the presence of a base, such as sodium bicarbonate. As the reaction products there are obtained 1-(2-chloroallyl)-2-nitroimidazole and, depending on the ratio of the starting materials azomycin and Y—(CH$_2$)$_n$—Y used, bis-(2-nitroimidazoles) of formula Ia and/or compounds of the formula

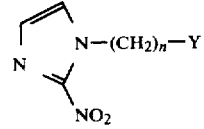

V wherein n and Y are as described above. The larger the excess of azomycin, the greater the amount of compound of formula Ia in the reaction mixture. The mixture of compounds of formulae Ia and V can be separated by procedures conventional in the art, for example, on the basis of their different solubilities, see Example 2. A compound of formula V can be converted into a compound of formula Ia by further reaction with azomycin.

PROCEDURE B

Isomerization of a 2-nitroimidazole compound of the formula

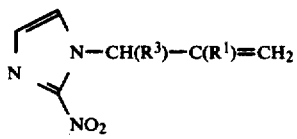

II wherein $R^1$ and $R^3$ are as described above, to produce a compound of the formula

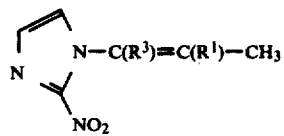

Ic wherein $R^1$ and $R^3$ are as described above. This isomerization can be carried out, for example, by treatment with acid, such as, sulfuric acid. The temperature is not critical, and isomerization is preferably carried out at room temperature.

PROCEDURE C

Cleaving off HX or HY from a 2-nitroimidazole of the formula

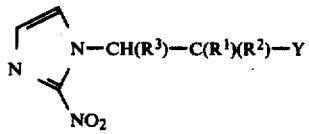

III or

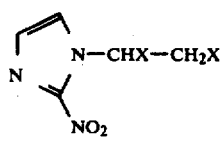

IV wherein $R^1$, $R^3$ and Y are as described above and X represents chlorine or bromine, to afford compounds of the formula

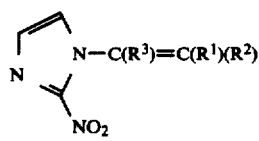

Ib or

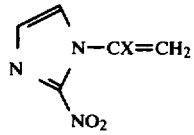

Id wherein $R^1$, $R^2$, $R^3$ and X are as described above.

The elimination of HX or HY can be carried out using procedures conventional in the art, for example, when Y represents halogen or tosyloxy by treatment with an alkali metal alcoholate in an inert organic solvent, preferably an alkanol. If the cleavable group denoted by Y in a compound of formula III is hydroxy, then this is conveniently firstly converted into a tosyloxy group. A compound of formula III in which Y represents hydroxy can, however, also be converted directly into a compound of formula Ib by treatment with a strong acid. Suitable acids include sulfonic acid, trifluoroacetic acid, sulfuric acid and the like.

PROCEDURE D

Attaching bromine to 2-nitro-1-vinylimidazole to obtain 1-(1,2-dibromoethyl)-2-nitroimidazole. This reaction is conveniently carried out in an inert organic solvent, such as dichloromethane, and while cooling with ice.

The starting materials of formula II can be prepared by reacting azomycin with a compound Y—CH(R$^3$)—C(R$^1$)=CH$_2$ or by cleaving HY from a compound of the formula

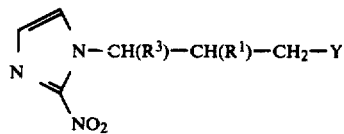

VI wherein $R^1$, $R^3$ and Y are as described above. The preparation of the compounds of formula VI can be carried out in analogy to the method for the preparation of a compound of formula V described in Procedure A. The cleavage of HY from a compound of formula VI can be carried out in analogy to the methods described in Procedure C.

The compounds of formula I of the present invention exhibit micro-filaricidal and especially macro-filaricidal activity. For example, in connection with macro-filaricidal activity, 1,2-ethylene-bis-(2-nitroimidazole) and 2-nitro-1-vinylimidazole exhibit average ED$_{90}$ values against Litomosoides carinii in the cotton rat of 147 mg/kg and 12 mg/kg, respectively. Therefore, the compounds of formula I and formula VII are useful therapeutically as filaricides. For such use the compounds of formula I and VII are administered as pharmaceutically acceptable compositions in combination with pharmaceutically acceptable, therapeutically inert inorganic or organic carrier materials. Such compositions may be in solid form, for example, tablets, dragees or capsules, or may be in liquid form, that is, as solutions, suspensions or emulsions.

Suitable art-recognized therapeutically inert pharmaceutical carrier materials useful in the preparation of the compositions of the present invention include, for example, water, gelatin, gum arabic, lactose, starch, talc, magnesium stearate, vegatable oils, polyalkyleneglycols, and the like. The pharmaceutical compositions of the present invention may be sterilized and may contain art-recognized adjuvants, for example, preservatives, stabilizers, wetting or emulsifying agents, agents for flavor improvement, salts to adjust osmotic pressure, buffers, and the like. The pharmaceutical compositions can be prepared by conventional procedures recognized in the art.

Compositions containing the 2-nitroimidazole compounds of formula I and VII can be utilized in the therapeutic treatment of filariasis in a considerable range of dosage depending on the individual clinical condition. Factors which may influence the dosage range include the type and severity of the infection and the activity of the specific compound administered. Generally, however, it is contemplated that a sufficient amount of such a composition be administered orally to provide about 5–150 mg/kg body weight per day, administered in one or more individual doses and for up to one week.

The following Examples further illustrate the present invention.

EXAMPLE 1

56 g of azomycin and 84 g of sodium bicarbonate were boiled under reflux for 6 hours in 300 ml of dimethylformamide and 47 g of 1,2-dibromoethane. The mixture was poured into 1500 ml of ice/water and the precipitate was filtered off. Recrystallization from 650 ml of nitromethane yielded 36 g of 1,2-ethylene-bis-(2-nitroimidazole), m.p. 248°–250° C. (decomposition).

EXAMPLE 2

206 g of 1-(2-iodoethyl)-2-nitroimidazole were boiled under reflux for 1 hour in a solution of 41 g of sodium methylate in 2 liters of methanol. The solution was evaporated under reduced pressure and the residue was taken up with 2 liters of ethyl acetate and 1 liter of water. The organic phase was washed twice with 0.5 liters of 10% sodium chloride solution each time and evaporated to dryness. After recrystallization from diisopropyl ether, the residue yielded 98.2 g of 2-nitro-1-vinyl-imidazole, m.p. 64°–66° C.

The starting material was prepared as follows:

340 g of azomycin and 510 g of sodium bicarbonate were stirred at 100° C. for 2 hours in 2000 ml of dimethylformamide and 1200 g of 1,2-dichloroethane. After cooling, the mixture was filtered, the bulk of the solvent was removed in a water-jet vacuum at a bath temperature of about 60° C. and the residue was stirred with 4 liters of ethyl acetate. 1,2-Ethylene-bis-(2-nitroimidazole) separated as a difficulty soluble crystalline product, which was filtered off and recrystallized from 700 ml of nitromethane; yield 56.5 g; m.p. 248°–250° C. (decomposition).

The filtrate was washed three times with 1 liter of 10% sodium chloride solution each time and evaporated under reduced pressure. Crystallization from 1 liter of ethyl acetate yielded 395 g of 1-(2-chloroethyl)-2-nitroimidazole, m.p. 85°–87° C.

163.4 g of 1-(2-chloroethyl)-2-nitroimidazole and 200.4 g of sodium iodide were heated under reflux for 4.5 hours in 1 liter of ethyl methyl ketone. After cooling, the mixture was filtered, the solvent was evaporated off, the residue was partitioned between 2 liters of dichloromethane and 1 liter of water and the organic phase was washed twice with 1 liter of water each time and evaporated. Crystallization from 1 liter of isopropanol yielded 206 g of 1-(2-iodoethyl)-2-nitroimidazole, m.p. 79°–82° C.

EXAMPLE 3

92 g of p-toluenesulphonyl chloride were added portionwise, while cooling with ice, to a solution of 69.5 g of 2-(2-nitro-1-imidazolyl) ethanol in 400 ml of pyridine. After standing overnight at room temperature, the mixture was poured into a mixture of 750 g of ice and 250 ml of concentrated hydrochloric acid. The precipitated tosylate was filtered off under suction and recrystallized from isopropanol to yield 73 g; m.p. 103°–105° C.

31.3 g of the tosylate were dissolved in 300 ml of toluene and, while cooling with ice, treated with 51.2 ml of a 2.15 N solution of sodium tert. amylate in toluene. Then, the mixture was poured into 300 ml of 0.7 N hydrochloric acid, the aqueous phase was separated, the organic phase was washed with 10% sodium chloride solution and concentrated to dryness under reduced pressure. The residue, recrystallized from isopropyl ether, yielded 9.5 g of 2-nitro-1-vinylimidazole, m.p. 62°–63° C.

EXAMPLE 4

21.8 g of azomycin in 120 ml of dimethylformamide were reacted at 100° C. for 5 hours with 32.5 g of sodium bicarbonate and 17.5 g of methallyl chloride. Subsequently, the mixture was poured into 1 liter of water and the precipitated 1-(2-methylallyl)-2-nitroimidazole was filtered off under suction; yield 12.1 g; m.p. 49°–51° C. An additional 13.8 g of the compound could be obtained by extracting the filtrate with ethyl acetate.

23.8 g of 1-(2-methylallyl)-3-nitroimidazole were dissolved at room temperature in 110 ml of concentrated sulfuric acid. After 30 minutes, the mixture was poured into 1 liter of ice/water, neutralized with concentrated ammonia and suction filtered. Recrystallization from diisopropyl ether yielded 5.4 g of 1-(2-methylpropenyl)-2-nitroimidazole, m.p. 77°–79° C.

EXAMPLE 5

20.1 g of 1-(1,2-dibromoethyl)-2-nitroimidazole were heated under reflux for 1 hour in 132 ml of a 0.51 N solution of sodium ethylate in methanol. The mixture was evaporated and the residue was taken up with 250 ml of ethyl acetate and 100 ml of water. The organic phase was washed with 100 ml of 10% sodium chloride solution and evaporated, and the residue was chromatographed on 300 g of silica gel using ethyl acetate/cyclohexane (4:1, v/v). After a forerun of 420 ml, there were isolated from 270 ml of further eluate 8.2 g of 1-(1-bromovinyl)-2-nitroimidazole; yield 4.6 g; m.p. 80°–82° C. (from isopropanol).

EXAMPLE 6

A solution of 24 g of bromine in 75 ml of dichloromethane was added dropwise, while stirring and cooling with ice, to a solution of 21 g of 2-nitro-1-vinylimidazole in 150 ml of dichloromethane. After 5 hours, the mixture was filtered and the filtrate was evaporated to dryness in a rotary evaporator. The residue, recrystallized from ethanol/water with the addition of active carbon, yielded 34 g of 1-(1,2-dibromoethyl)-2-nitroimidazole, m.p. 102°–106° C.

EXAMPLE 7

Tablets containing the following ingredients were prepared by conventional procedures:

| | |
|---|---|
| 1,2-Ethylene-bis-(2-nitroimidazole) | 100 mg |
| Lactose | 192 mg |
| Maize starch | 80 mg |
| Hydrolysed maize starch | 20 mg |
| Calcium stearate | 8 mg |
| | 400 mg |

EXAMPLE 8

Tablets containing the following ingredients were prepared by conventional procedures:

| | |
|---|---|
| 2-Nitro-1-vinylimidazole | 50 mg |
| Lactose | 194 mg |
| Pregelatinised maize starch | 150 mg |
| Calcium stearate | 6 mg |
| | 400 mg |

We claim:

1. A method for the treatment of filariasis which comprises administering to a host requiring such treatment an amount effective therefor of a compound of the formula

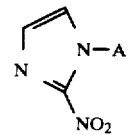

wherein A is one of the groups

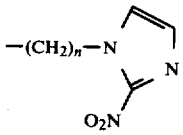

$-C(R^3)=C(R^1)$ $(R^2)$, $-CHBr-CH_2Br$ or $-CH_2-CCl=CH_2$ or $R^4$; n is 1,2,3 or 4; $R^1$ and $R^2$ are hydrogen or $C_{1-3}$-alkyl and $R^3$ is hydrogen $C_{1-3}$-alkyl, chlorine or bromine and $R^4$ is $-CH_2-CH_2OH$, $-CH_2-CHOH-CH_2OCH_3$, $-CH_2-CHOH-CH_2OH$ or

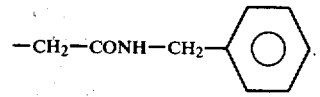

* * * * *